United States Patent [19]
McGuffin

[11] 3,993,044
[45] Nov. 23, 1976

[54] METHOD AND DEVICE FOR DETERMINING THE LENGTH OF A ROOT CANAL OF A TOOTH

[76] Inventor: William G. McGuffin, 38 Clearwater Drive, Willingboro, N.J. 08046

[22] Filed: Mar. 10, 1975

[21] Appl. No.: 556,667

[52] U.S. Cl. .............................. 128/2 S; 32/40 R; 32/57; 33/174 D; 128/2.1 Z
[51] Int. Cl.² .......................................... A61B 5/05
[58] Field of Search .......... 128/2 S, 2 N, 2 R, 2.1 Z; 32/40 R, 57, 2.1 Z; 33/174 D

[56] References Cited
UNITED STATES PATENTS

| 3,058,225 | 10/1962 | Ward | 128/2 S |
|---|---|---|---|
| 3,199,024 | 8/1965 | Manly et al. | 324/57 H |
| 3,320,946 | 5/1967 | Dethloff et al. | 128/2.1 Z |
| 3,660,901 | 5/1972 | Inoue | 128/2 S X |
| 3,753,434 | 8/1973 | Pike et al. | 128/2.1 Z |
| 3,901,216 | 8/1975 | Felger | 128/2.1 Z |

*Primary Examiner*—Kyle L. Howell
*Attorney, Agent, or Firm*—Carl P. Steinhauser

[57] ABSTRACT

A method and device for measuring the length of a root canal of a tooth in which a reference signal obtained by placing an electrode or terminal of an oscillator in the gingival tissue and a signal obtained by inserting an electrode or terminal of an oscillator into the root canal are phase locked and mixed in a product detector to produce an electrical quantity indicative of the length of the root canal.

8 Claims, 7 Drawing Figures

METHOD AND DEVICE FOR DETERMINING THE LENGTH OF A ROOT CANAL OF A TOOTH

This invention relates to a method and device for measuring the length of a root canal of a tooth.

In a previously described method of determining the length of root canals (see J. CANAD DENTAL ASSN., No. 9, 1973) a probe is placed into the gingival sulcus and the machine (see U.S. Pat. No. 3,660,901) tuned to the proper frequency. As the sulcus is first entered, the machine emits a series of beeps which increase in length and pitch as the probe moves further into the sulcus. At a depth of about 0.5 mm the sound becomes continuous. This first continuous sound is the sound to which the pitch of the reference tuner is adjusted using a dial on the face of the instrument. This sound is called the reference sound since it is used as a standard against which the probe sound is compared.

The probe is then placed into the canal to be measured. The operator will hear a similar series of sounds. As the probe enters the canal there will be a short beeping sound, and as the tip of the probe reaches nearer the apex the sound increases in duration and pitch. When the apex is reached the sound heard is continuous, and the pitch is identical to the reference sound established above.

It is an object of this invention to determine the apex location of a root canal of a tooth with greater precision and less ambiguity.

It is a further object of the invention to provide a method and device for locating the apex location of a root canal of a tooth without requiring an operator to compare the duration and pitch of sounds.

A further object of the invention is to provide a direct visual and/or audible indication when the apex location is reached.

These and further objects of the invention will appear as the specification progresses.

In accordance with this invention, the frequency of a reference oscillator which is established as described above by inserting a probe into the gingival suculus is compared with the frequency of an oscillator connected to a probe which is inserted into the root canal. As the apex is reached, the frequency of the oscillator coupled to the probe as it is inserted into the canal changes. The probe signal and reference signal are continuously compared in a phase detector, commonly called a product detector. When the apex is reached, the oscillators which are loosely coupled are locked in synchronism and the output of the phase detector is used, either audibly or visually to indicate that the apex has been reached.

The invention will be described with reference to the drawings in which.

Figure 1:
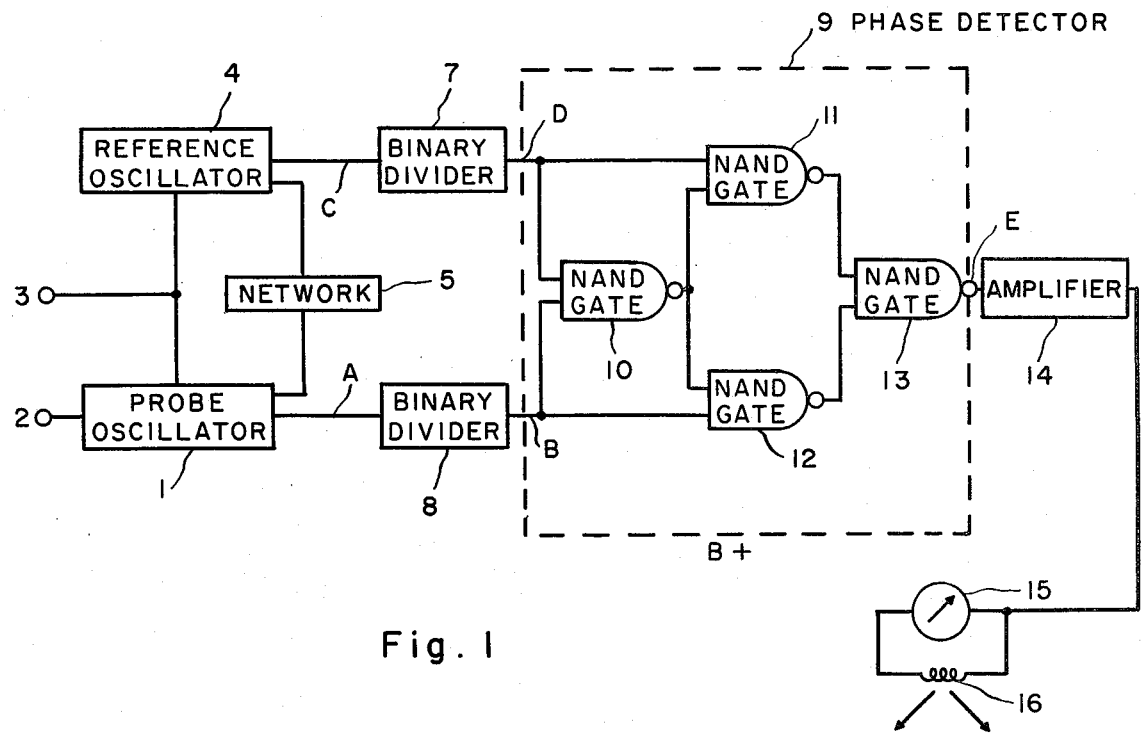
FIG. 1 is a block diagram of the device for locating the apex of the root canal of a tooth.

FIGS. 4a-d show phase differences between the probe and reference oscillator as the probe approaches the apex of the tooth.

For the purpose of measuring the length of a root canal it is first necessary to establish a reference frequency and this is accomplished by connecting probe oscillator 1 to a terminal 2 which is inserted into gingival tissue or gingival suculus with a terminal 3 providing a return path placed against the outer tissue (oral mucus membrane). The frequency of this oscillator will be determined by the impedance of the gingival tissue. A second oscillator 4, a reference oscillator loosely coupled with oscillator 1 by network 5, is adjusted using a dial on the face of the instrument to provide the output indication which indicates that the reference oscillator is phase locked with the first or probe oscillator. At this point the reference oscillator will be of the same frequency and phase as the probe oscillator, hence forth to be used as a reference indicative of the impedance of the gingival tissue.

Figure 2:
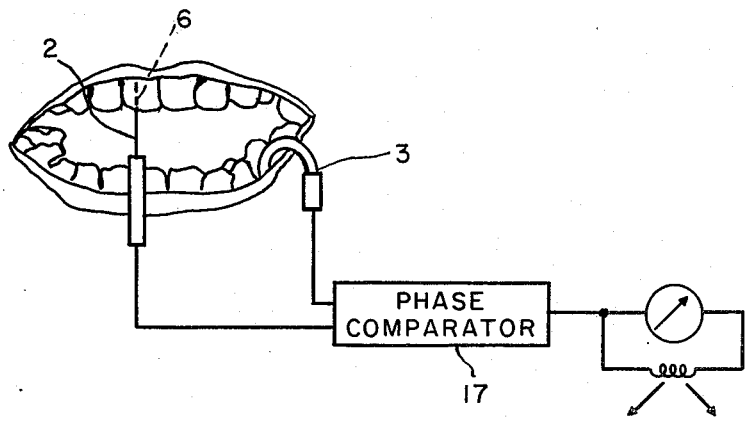
FIG. 2 shows the device used for measuring the length of a root canal.

Terminal 2 connected to probe oscillator 1 is inserted into the root canal 6 (see FIG. 2) of a tooth. The frequency of oscillator 1 will vary as the terminal 2 is inserted deeper into the root canal approaching that of oscillator 4 when the apex of the canal is reached.

The outputs of the respective oscillators are coupled to binary dividers 7 and 8, which may be conventional flip-flops. The binary dividers provide output signals of near absolute symmetry, a necessary condition for the proper operation of the phase detector 9.

The outputs of the binary dividers are applied to an array of logic gates 10, 11, 12 and 13 interconnected to form phase detector 9 which, as generally understood by those skilld in the art, is commonly known as an Exclusive-Or gate: a logic circuit which has an output at a first voltage level when both of its inputs are at a like voltage level and an output at a second voltage level when its two inputs are at different voltage levels. The phase detected output of logic gate 13 is amplified by amplifier 14 which is connected to meter 15 for visual indication and/or loudspeaker 16 for generating an audible tone.

The terminals 2 and 3 comprise respectively a probe and lip hook, the tip of the probe being insertable into the root canal 6 while the lip hook rests against the outer tissue (oral mucus membrane).

As the tip 2 of the probe is inserted into the root canal, the frequency of oscillator 1 changes which when compared with the frequency of oscillator 4 in phase detector 9 (17 in FIG. 2 which includes the oscillator and binary dividers) results in a phase difference which when amplified gives a visual or audible indication. When the probe tip reaches the apex, the frequencies will be the same, and the phase detector will lock so that the output will be a null. This will be shown by the meter pointer returning to zero, and the absence of an audible signal.

Figure 3:
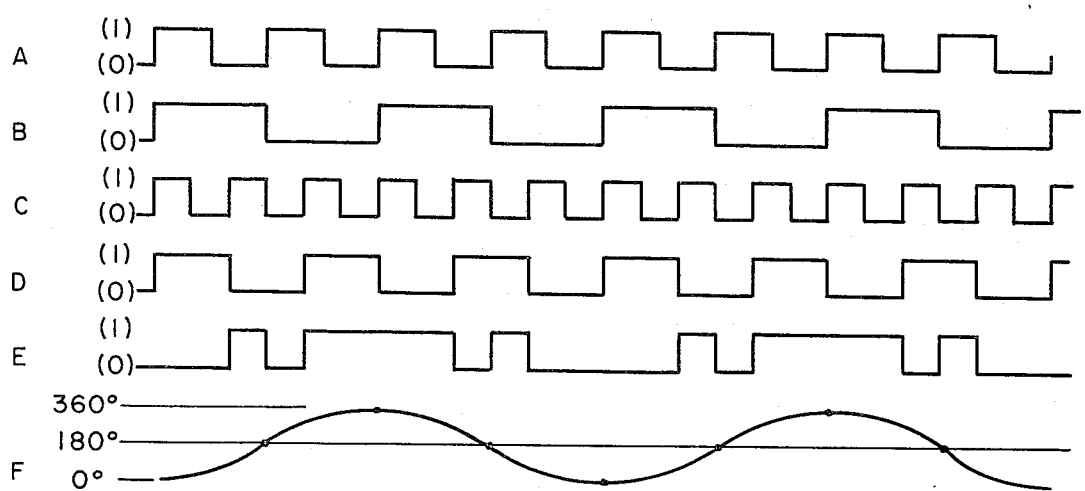
FIG. 3 shows wave forms for a probe approaching the apex of a tooth.

In the operation of the circuit of FIG. 1, the output of the probe oscillator (1) shown as wave form A in FIG. 3 is a square wave (not necessarily symmetrical) at one binary value representing a 1 during the positive half period and at the other binary value representing a 0 during the negative half period. Likewise, the output of the reference oscillator shown as wave form C is a square wave alternating between the two binary values, 1 and 0. FIG. 3 depicts the circuit wave forms for a condition when the probe (2) is not at, but is approaching the apex of the tooth. In this circumstance the probe oscillator, wave form A, is lower in frequency than the reference oscillator, wave form C. The outputs of their respective binary dividers, B and D, are likewise of different frequencies, but do exhibit a symmetry which is independent of any asymmetry in their respective inputs. Wave form E of FIG. 3 depicts the output of the phase detector (Exclusive-Or gate) when the two inputs are not phase locked. As is understood in the art, this Exclusive-Or gate produces an output representing a 1 when one input represents a 1 and the other a 0, and an output representing a 0, when both inputs represent the same binary value — either 1,1 or 0,0. Wave form F is simply a representation of the phase rotation occuring between the probe and reference oscillator outputs manifesting itself as a low frequency modulation of the visual indicator and a warbling in the audible indication.

Figure 4A:
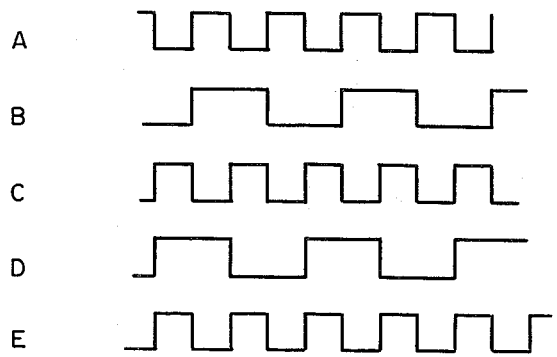

FIG. 4a depicts the same wave forms for a condition when the probe has moved much closer to the apex of the tooth. In this figure the two oscillators are phase locked for the first time; this phase lock which occurs short of the apex is not an in-phase (zero phase) condition. As depicted, the phase difference of the probe (A) and reference (C) oscillators is approximately 180° (normally this initial phase lock will occur with a phase difference between 90° and 180°). The resultant output of the phase detector (E) is a constant signal with a frequency equal to that of the equal probe and reference oscillators.

Figure 4B:
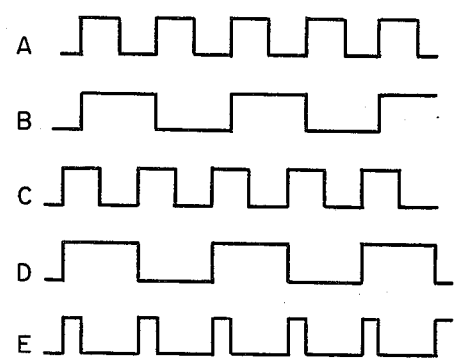
Figure 4C:
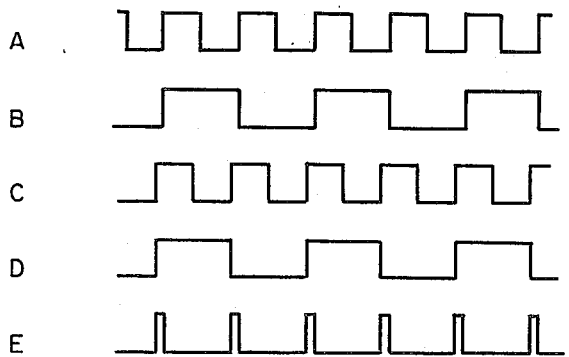
Figure 4D:
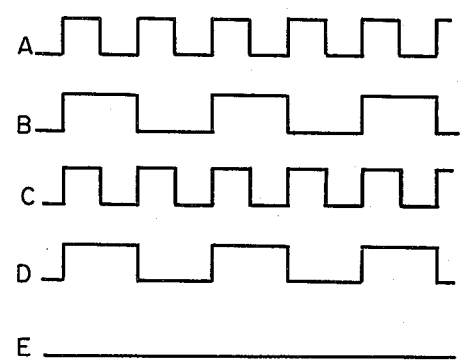

As the probe proceeds nearer the apex this phase difference between the probe and reference oscillators gradually decreases to zero. FIGS. 4b, 4c, and 4d illustrate this action. FIG. 4b depicts a phase difference of approximately 90° and the phase detector output (E), although of the same frequency as that of FIG. 4a, is of diminished amplitude. FIG. 4c depicts the condition when the probe is extremely near the apex. In this figure the phase difference is almost zero and the fundamental frequency component of wave form E is greatly diminished.

Finally, in FIG. 4d, the probe is at the apex of the tooth, the phase difference between the probe and reference oscillators is zero, the output of the phase detector (wave form E) is zero, the resulting meter deflection is zero, and the audible indication is absent.

It is apparent that this aproach is more sensitive than the heretofore described techniques and allows the operator to accurately locate the apex of the root canal. Furthermore, should the operator inadvertently penetrate past the apex of the tooth he will be instantly alerted by the reappearance of both the visual and audible indicators; for, as the probe passes the apex of the tooth, the sequence described in FIGS. 4a, 4b, 4c and 4d reverses, and the phase difference between probe and reference oscillators increases as the probe moves away from the apex.

Although, the invention embodied in FIG. 1 employs "NAND" logic in its implementation, it is recognized and understood that the invention could be implemented equally as well with any conventional logic (i.e., NOR, AND, OR, ETC).

What I claim is:

1. A device for locating the apex of a root canal of a tooth comprising a probe positionable within a root canal of a tooth, a first oscillator adapted to be coupled to soft tissue surrounding teeth for establishing a reference signal having a given frequency corresponding to a frequency produced by inserting the probe into the root canal and reaching the apex thereof, a second oscillator coupled to the probe the frequency of which is determined by the position of the probe inside the root canal, means to produce a voltage proportional to the phase difference between the frequencies of the first oscillator and second oscillators, and means responsive to said voltage to produce an indication of the position of the probe in the root canal.

2. A device as claimed in claim 1 in which the means to produce a voltage proportional to the phase difference between the first oscillator and the second oscillator is a phase detector.

3. A device as claimed in claim 2 in which each oscillator is connected to the phase detector through a binary divider.

4. A device as claimed in claim 2 in which the indicating means is a visual indicating means.

5. A device as claimed in claim 2 in which the indicating means is an audible means.

6. A method of locating the apex of a root canal of a tooth comprising the steps of inserting a probe into the root canal of a tooth, connecting a first oscillator to the probe, connecting a second oscillator to the probe while at the apex of the root canal to fix the frequency thereof and then to gingival tissue surrounding a tooth, moving the probe within the root canal to change the frequency of said first oscillator, comparing the frequencies of the first and second oscillators to determine the phase difference therebetween, and producing an indication of said phase diffference to determine the location of the probe.

7. A method as claimed in claim 6 in which the indication produced is visual.

8. A method as claimed in claim 6 in which the indication produced is audible.

* * * * *